US00PP25644P2

(12) United States Plant Patent
Beekenkamp

(10) Patent No.: US PP25,644 P2
(45) Date of Patent: Jun. 23, 2015

(54) ***BEGONIA* PLANT NAMED 'BKPBEBVWT'**

(50) Latin Name: *Begonia boliviensis*
Varietal Denomination: BKPBEBVWT

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 146 days.

(21) Appl. No.: 13/986,828

(22) Filed: Jun. 10, 2013

(51) Int. Cl.
*A01H 5/00* (2006.01)

(52) U.S. Cl.
USPC ..... Plt./343

(58) Field of Classification Search
USPC ..... Plt./343
See application file for complete search history.

*Primary Examiner* — Susan McCormick Ewoldt
(74) *Attorney, Agent, or Firm* — C. A. Whealy

(57) ABSTRACT

A new and distinct cultivar of *Begonia* plant named 'BKPBEBVWT', characterized by its upright to somewhat outwardly spreading and mounded plant habit; freely basal branching habit; dark green-colored leaves; freely flowering habit; and single white-colored flowers.

2 Drawing Sheets

Botanical designation: *Begonia boliviensis.*
Cultivar denomination: 'BKPBEBVWT'.

BACKGROUND OF THE INVENTION

The present invention relates to a new and distinct cultivar of *Begonia* plant, botanically known as *Begonia boliviensis* and hereinafter referred to by the name 'BKPBEBVWT'.

The new *Begonia* plant is a product of a planned breeding program conducted by the Inventor in Maasdijk, The Netherlands. The objective of the breeding program was to develop new compact and freely branching and freely flowering *Begonia* plants with attractive flower colors.

The new *Begonia* plant originated from a cross-pollination made by the Inventor in September, 2010 of a proprietary selection of *Begonia boliviensis* identified as code number 10-021-12, not patented, as the female, or seed, parent with a proprietary selection of *Begonia boliviensis* identified as code number 10-000-11, not patented, as the male, or pollen, parent. The new *Begonia* plant was discovered and selected by the Inventor as a single flowering plant from within the progeny of the stated cross-pollination in a controlled greenhouse environment in Maasdijk, The Netherlands in May, 2011.

Asexual reproduction of the new *Begonia* plant by tip cuttings in a controlled greenhouse environment in Maasdijk, The Netherlands since June, 2011 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEBVWT'. These characteristics in combination distinguish 'BKPBEBVWT' as a new and distinct *Begonia* plant:

1. Upright to somewhat outwardly spreading and mounded plant habit.
2. Freely basal branching habit.
3. Dark green-colored leaves.
4. Freely flowering habit.
5. Single white-colored flowers.

Plants of the new *Begonia* can be compared to plants of the female parent selection. Plants of the new *Begonia* differ primarily from plants of the female parent selection in the following characteristics:

1. Plants of the new *Begonia* have single flowers whereas plants of the female parent selection have double flowers.
2. Plants of the new *Begonia* have darker-colored leaves than plants of the female parent selection.
3. Plants of the new *Begonia* have shorter peduncles than plants of the female parent selection.

Plants of the new *Begonia* can be compared to plants of the male parent selection. Plants of the new *Begonia* differ primarily from plants of the male parent selection in the following characteristics:

1. Plants of the new *Begonia* are more freely branching than plants of the male parent selection.
2. Plants of the new *Begonia* have slightly smaller flowers than plants of the male parent selection.
3. Flower tepals of plants of the new *Begonia* are white in color whereas flower tepals of plants of the male parent selection are off-white in color.

Plants of the new *Begonia* can be compared to plants of the *Begonia boliviensis* 'Crackling Fire White', not patented. In side-by-side comparisons conducted in Maasdijk, The Netherlands, plants of the new *Begonia* differed from plants of 'Crackling Fire White' in the following characteristics:

1. Plants of the new *Begonia* were more freely branching than plants of 'Crackling Fire White'.
2. Plants of the new *Begonia* had slightly smaller flowers than plants of 'Crackling Fire White'.

3. Flower tepals of plants of the new *Begonia* were white in color whereas flower tepals of plants of 'Crackling Fire White' were off-white in color.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKPBEBVWT' grown in a container.

The photograph on the second sheet are close up views of typical flowers and leaves of 'BKPBEBVWT'.

DETAILED BOTANICAL DESCRIPTIONS

Plants used for the aforementioned photographs and the following observations and measurements were grown in 12-cm containers during the winter in a glass-covered greenhouse in Maasdijk, The Netherlands. During the production of the plants, day temperatures ranged from 19° to 20° C., night temperatures ranged from 18° to 19° C. and light levels averaged 6,000 lux. Plants were eight weeks old when the photographs and the description were taken. In the following description, color references are made to The Royal Horticultural Society Colour Chart, 2007 Edition, except where general terms of ordinary dictionary significance are used.

Botanical classification: *Begonia boliviensis* 'BKPBEBVWT'.

Parentage:

*Female, or seed, parent*.—Proprietary selection of *Begonia boliviensis* identified as code number 10-021-12, not patented.

*Male, or pollen, parent*.—Proprietary selection of *Begonia boliviensis* identified as code number 10-000-11, not patented.

Propagation:

*Type*.—By tip cuttings.

*Time to initiate roots, summer and winter*.—About 20 days at temperatures about 25° C.

*Time to produce a rooted young plant, summer and winter*.—About 35 to 36 days at temperatures about 21° C. to 23° C.

*Root description*.—Fine, fibrous; light brown in color; plants of the new *Begonia* have not been observed to form tubers.

*Rooting habit*.—Moderate branching; medium density.

Plant description:

*Plant and growth habit*.—Upright, somewhat outwardly spreading and mounded plant habit; plant shape, spreading to flattened globular; freely basal branching with about seven basal branches per plant; moderately vigorous growth habit.

*Plant height*.—About 13.8 cm.

*Plant width*.—About 19.2 cm.

*Lateral branch description*.—Length: About 5.2 cm. Diameter: About 4 mm. Internode length: About 1.1 cm. Texture: Sparsely hirsute. Aspect: About 40° from the vertical. Color, developing: Close to 146D. Color, developed: Close to between 148A and 152B.

*Leaf description*.—Arrangement: Alternate, simple. Length: About 7.4 cm. Width: About 2.6 cm. Shape: Lanceolate to narrowly ovate, asymmetrical. Apex: Long and narrowly acuminate. Base: Oblique. Margin: Bi-serrate. Texture, upper surface: Sparsely pubescent; velvety. Texture, lower surface: Sparsely pubescent. Venation pattern: Laciniate. Color: Developing leaves, upper surface: Close to N137C to N137D. Developing leaves, lower surface: Close to 148A heavily tinged with close to 177A to 177B. Fully expanded leaves, upper surface: Darker than between 147A and N189A; venation, close to 137A to 137B. Fully expanded leaves, lower surface: Close to 183B; venation, close to 146B. Petioles: Length: About 2.6 cm. Diameter: About 2 mm. Texture, upper and lower surfaces: Smooth, glabrous. Color, upper surface: Close to 152C, distally tinged with close to 185A. Color, lower surface: Close to 152C.

Flower description:

*Flowering habit*.—Single flowers arranged in axillary pairs, typically one rotate female and one cruciform male flowers; freely flowering habit with about nine flowers per lateral branch and about 63 flowers developing per plant; flowers face outwardly to slightly drooping.

*Fragrance*.—None detected.

*Natural flowering season*.—Plants begin flowering about seven weeks after planting; long flowering period, plants flower freely and continuously from spring into the autumn in The Netherlands.

*Flower longevity*.—Individual flowers last about ten days on the plant; flowers not persistent.

*Inflorescence height*.—About 6.7 cm.

*Inflorescence diameter*.—About 5.5 cm.

*Female flowers*.—Flower diameter: About 3.4 cm. Flower height: About 3.9 cm. Flower buds: Length: About 2.3 cm. Diameter: About 6 mm to 12 mm. Shape: Ovate, flattened. Color: Close to 159A tinged with close to 65C to 65D; towards the base, close to 145B. Tepals: Quantity per flower and arrangement: Five in a single whorl. Length: About 3.2 cm. Width: About 1.4 cm. Shape: Oblanceolate to obovate. Apex: Acute. Margin: Entire. Texture, upper and lower surfaces: Smooth, glabrous; velvety. Color: When opening, upper surface: Close to NN155C; towards the margins, slightly tinged with close to 62D; towards the base, close to 145C. When opening, lower surface: Close to NN155B; towards the margins, slightly tinged with close to 62D; towards the base, close to 145C. Fully opened, upper and lower surfaces: Close to NN155A tinged with close to 62D; towards the base, close to 145C to 145D; with development tepals become more heavily tinged with close to 62D.

*Male flowers*.—Flower diameter: About 3.3 cm. Flower height: About 3.5 cm. Flower buds: Length: About 2 cm. Diameter: About 5 mm to 13 mm. Shape: Ovate, flattened. Color: Close to 157B; towards the margins, tinged with close to 49D. Tepals: Quantity per flower and arrangement: Four in a single whorl. Length: About 3.4 cm. Width: About 1.2 cm or 2 cm. Shape: Two tepals, ovate; and other two tepals, oblanceolate to narrowly oblong. Apex: Acute. Margin: Entire. Texture, upper and lower surfaces: Smooth, glabrous; velvety. Color: When opening, upper surface: Close to NN155C; towards the margins, slightly tinged with close to 62D; towards the base, close to 145C. When opening, lower surface: Close to NN155B; towards the margins, slightly tinged with close to 62D; towards the base, close to 145C. Fully opened, upper and lower surfaces: Close to NN155A tinged with close to 62D; towards the base, close to 145C to 145D; with development tepals become more heavily tinged with close to 62D.

*Peduncles*.—Length: About 3.7 cm. Diameter: About 2 mm. Angle: About 40° from branch axis. Strength: Flexible, bending with the weight of the flowers. Texture: Smooth, glabrous. Color: Close to 144A to 144B.

*Pedicels, female flowers*.—Length: About 2 cm. Diameter: About 1.5 mm. Angle: About 40° from the peduncle axis. Strength: Flexible, bending with the weight of the flowers. Texture: Smooth, glabrous. Color: Close to 152D.

*Pedicels, male flowers*.—Length: About 2 cm. Diameter: About 1.5 mm. Angle: Same as peduncle axis. Strength: Flexible, bending with the weight of the flowers. Texture: Smooth, glabrous. Color: Close to 152D.

*Reproductive organs*.—Androecium, present on male flowers only: Quantity of stamens per flower: About 25. Filament length: About 4 mm. Filament color: Close to 1A to 1B. Anther length: About 2 mm. Anther shape: Elliptic. Anther color: Close to 14B. Pollen amount: Scarce to moderate. Pollen color: Close to 11D. Gynoecium: Present on female flowers only. Quantity of pistils per flower: About six. Pistil length: About 1 cm. Style length: About 3 mm. Style color: Close to 1B. Stigma color: Close to 7B and 7C. Ovary color: Close to 144B; wings, close to N144D.

Disease & pest resistance: Resistance to pathogens and pests common to *Begonia* plants has not been observed on plants of the new *Begonia*.

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'BKPBEB-VWT' as illustrated and described.

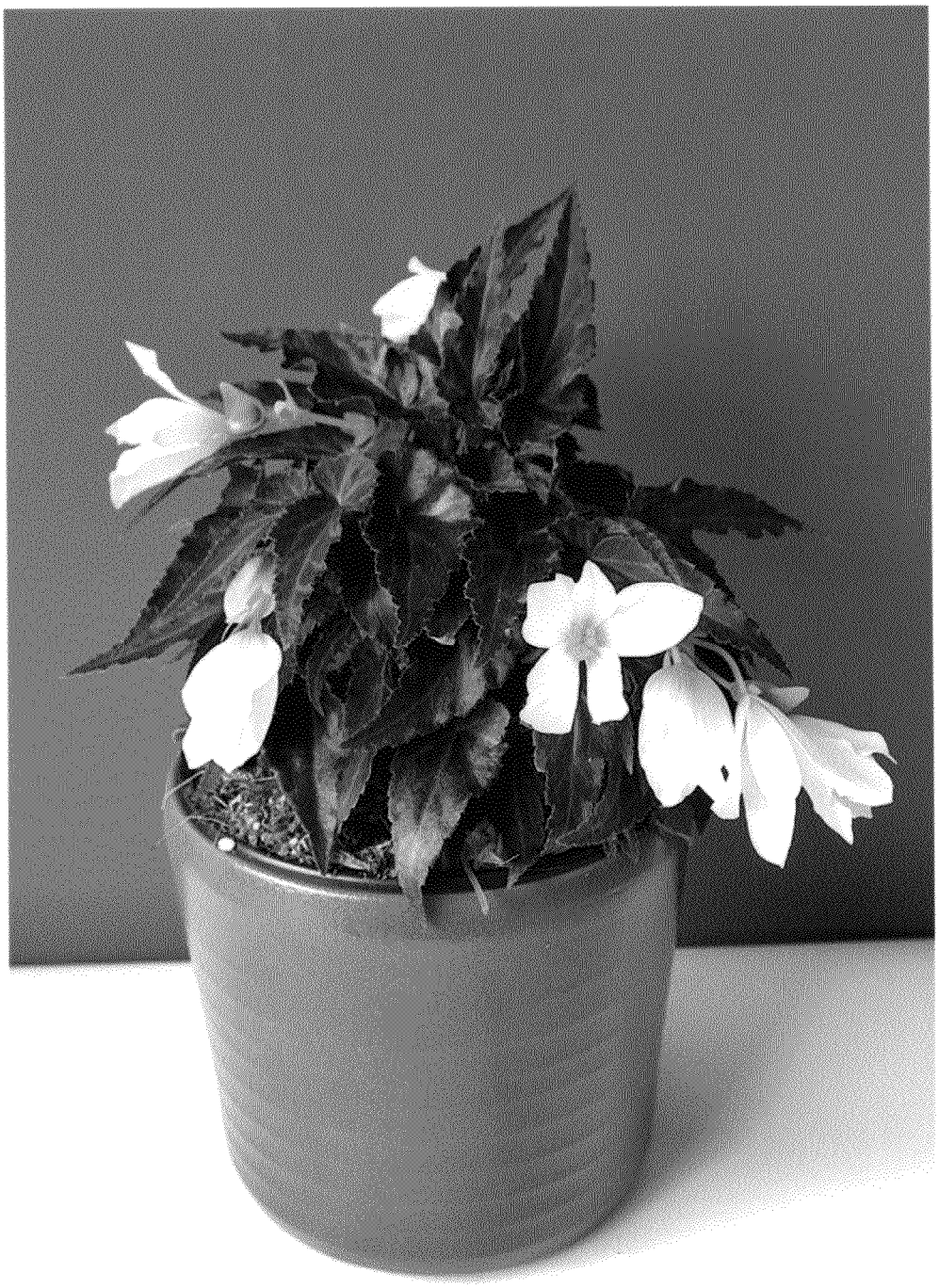

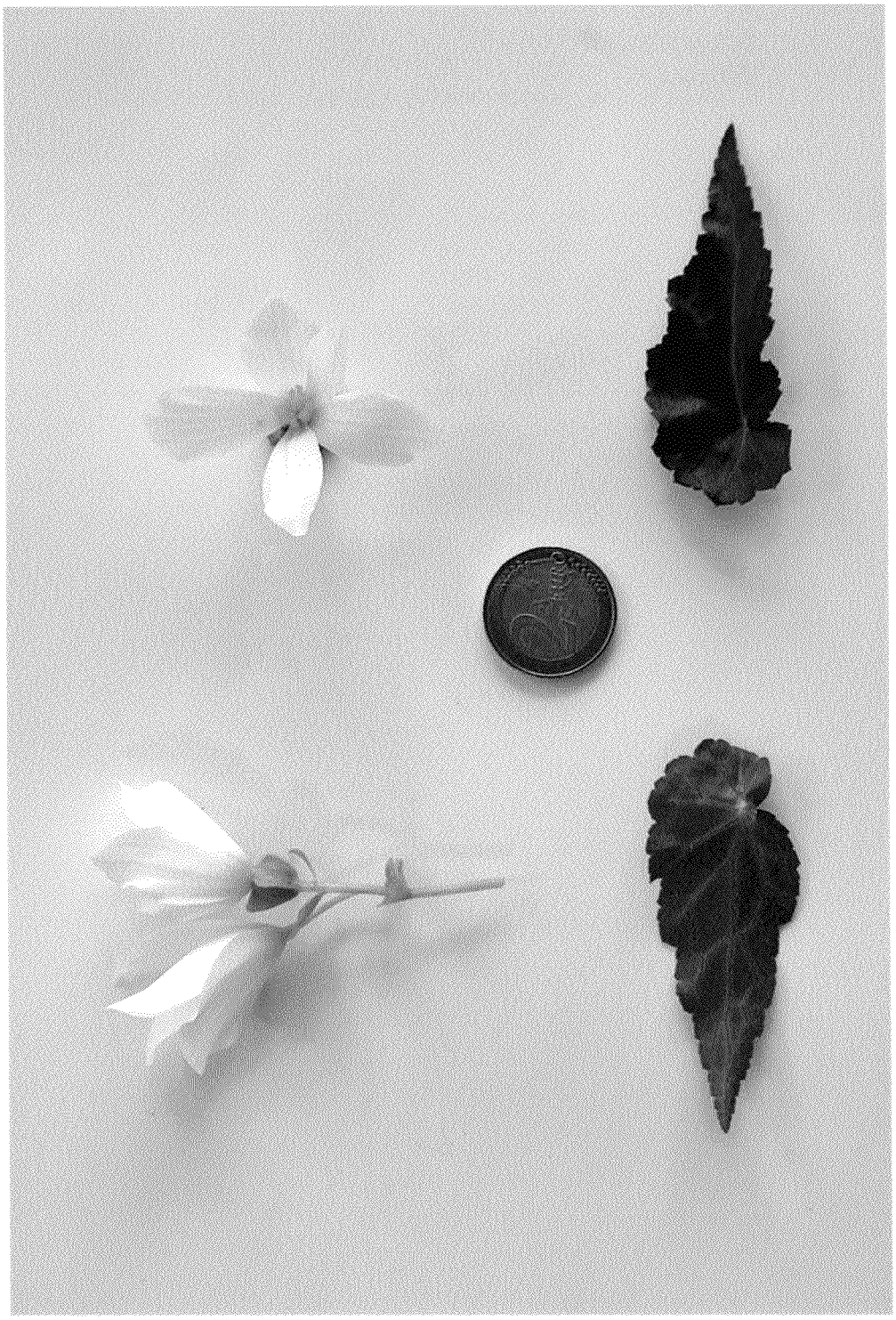

* * * * *